United States Patent [19]

Massof

[11] Patent Number: 4,848,898
[45] Date of Patent: Jul. 18, 1989

[54] APPARATUS FOR TESTING COLOR VISION

[75] Inventor: Robert W. Massof, Baltimore, Md.

[73] Assignee: LKC Technologies, Inc., Gaithersburg, Md.

[21] Appl. No.: 68,090

[22] Filed: Jun. 30, 1987

[51] Int. Cl.$^4$ .............................................. A61B 3/02
[52] U.S. Cl. .................................. 351/242; 351/243; 351/246
[58] Field of Search ................ 351/239, 242, 243, 246

[56] References Cited

U.S. PATENT DOCUMENTS

| | | |
|---|---|---|
| 1,658,356 | 2/1928 | Schaaff . |
| 1,973,966 | 9/1934 | Tillyer . |
| 2,453,335 | 11/1948 | Morris . |
| 2,937,567 | 5/1960 | Hardy et al. . |
| 3,382,025 | 5/1968 | Knoll . |
| 3,801,188 | 4/1974 | Hunt et al. . |
| 3,947,099 | 3/1976 | Grolman et al. . |
| 4,285,580 | 8/1981 | Murr .................................. 351/242 |

FOREIGN PATENT DOCUMENTS 2520604 1/1982 France .

OTHER PUBLICATIONS

"A Red-Green Anomaloscope Using Light Emitting iodes" by J. E. Saunders, Dec. 15, 1975, p. 872.
"A Solid State Anomaloscope" by S. J. Dain, G. Strange and R. Boyd, 1980, p. 182 of Chapter 4.
"Procedures for Testing Color Vision" by Committee on Vision Assembly of Behavioral and Social Sciences National Research Council, 1981, Chapter 3.
"Procedures for Testing Color Vision" by Committee on Vision Assembly of Behavioral and Social Sciences National Research Council, 1981, Chapter 3.

Primary Examiner—William L. Sikes
Assistant Examiner—J. P. Ryan
Attorney, Agent, or Firm—Pollock, VandeSande & Priddy

[57] ABSTRACT

To provide for an easy and accurate color vision tester, a plurality of yellow, red and green lights are mounted, or projected, onto a display, with the yellow lights providing for the background luminance while the red and green lights providing for a mixture of red and green luminance. Different patterns on the display are formed by a combination of the red and green lights. A particular pattern can be selected from among the various patterns by a pattern select circuit. The intensity of the red to green lights can be inversely varied so that different ratios of intensity for the selected pattern may be presented to an observer. Each of these ratios corresponds to a certain type of color vision. Therefore, by determining whether an observer is able to discern the pattern from the background in a particular intensity setting, the type of color vision an observer has can easily be ascertained.

20 Claims, 2 Drawing Sheets

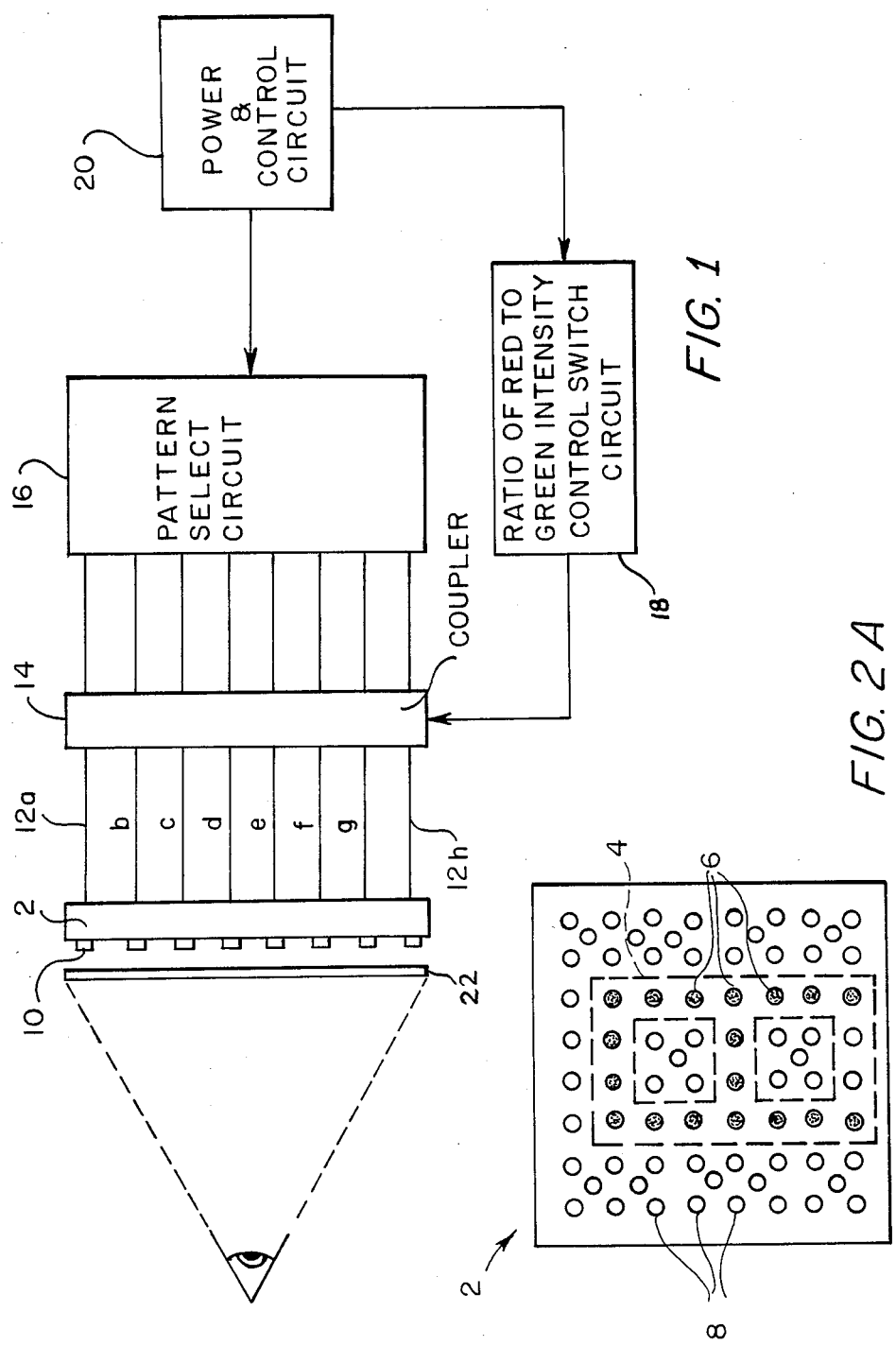

APPARATUS FOR TESTING COLOR VISION

FIELD OF THE INVENTION

The present invention relates to color vision testers and more particularly to a tester which can easily identify a type of color vision deficiency and the degree of deficiency, if any, an observer has.

BACKGROUND OF THE INVENTION

As is well known, the human visual system is trichromatic. All colors can be matched by a mixture of three primary colors: red, green, and blue. This trichromatic property of human color vision is a consequence of three different photoreceptor types in the retina: the R receptor (maximally sensitive to the red end of the spectrum), the G receptor (maximally sensitive to the middle, or green part of the spectrum), and the B receptor (maximally sensitive to the blue end of the spectrum). The ratios of red, green, and blue primaries in a color mixture that is made to match some arbitrary color is determined by the spectral absorption characteristics of the photopigments in the three types of receptors.

Approximately 8% of males and 0.2% of females have abnormal color vision due to a defect inherited on the X chromosome. One form of color vision defect, called anomalous trichromacy, is characterized by abnormal spectral absorption characteristics of the R receptor photopigment (protanomalous trichromat) or of the G receptor photopigment (deuteranomalous trichromat). Anomalous trichromats still require 3 primary colors in a mixture to perform color matching, however, the ratio of the primaries are anomalous in comparison to the normal population. A second form of color vision defect, called dichromacy, is characterized by an absence of the R receptor photopigment (protanope) or an absence of the G receptor photopigment (deuteranope). Protanopes and deuteranopes equire only two primary colors in a mixture to perform color matching.

X-linked color vision defects are diagnosed on the basis of tests that are standardized against color matching. In particular, a yellow light is matched by normal trichromats with a unique mixture of a red primary and a green primary. Relative to the normal match, protanomalous trichromats add too much red to the mixture and deuteranomalous trichromats add too much green to the mixture. Protanopes and deuteranopes match the red alone to the yellow, green alone to the yellow, and any ratio of red to green in a mixture to the yellow. The major difference between protanopes and deuteranopes is in their sensitivity to colored lights. Protanopes are very insensitive to red light, consequently red lights appear much dimmer than do yellow or green lights that look to be the same brightness for normals. Deuteranopes have the same sensitivity to colors as does the normal.

A prior art instrument which uses the above-stated principle for testing the color vision deficiency of an observer is give in Grolman, et al. U.S. Pat. No. 3,947,099. There an anomaloscope that uses a bipartite field having a spectrally pure yellow half and a mixture red and green half for testing the color vision of an observer is diclosed. However, the problem with this type of anomaloscope is that it is very difficult to use. For instance, in order to adjust the spectral red and green colors of the mixture on one half of a display circle to correspond with the spectrally pure yellow color on the other half of the display circle, the observer has to be both able to adjust the ratio of the red and green colors in the mixture and to adjust the brightness thereof so that it will look just like the spectral yellow color. Accordingly, since such anomaloscope is so difficult to use, most clinicians, in testing a color vision patient, would resort to the use of pseudoisochromatic plates, an example of which is given in Hardy, et al. U.S. Pat. No. 2,937,567. Briefly, the pseudoisochromatic plates are books that have printed patterns embedded in backgrounds of different colors. The printed patterns are in different hues of red and green colors. However, these hues are not calibrated. Thus, although the plates are very easy to use, since the patient observer only needs to look at the different plates and inform the clinician when he sees a figure, the plates do not have the precision, in terms of determining the type and degree of color vision a patient has, of an anomaloscope.

There exists, therefore, a need for an instrument that can provide for both easy operation and precise measurements of a patient observer's color vision.

BRIEF DESCRIPTION OF THE INVENTION

The present invention is able to fulfil the abovestated need by utilizing a plurality of yellow, red and green lights on a viewing display. Specifically, the yellow lights are randomly spaced while the red and green lights, although likewise randomly spaced, are combined in such a way so as to form a multiple number of prearranged patterns on the display. A predetermined number of the thus combined red and green lights are selectively turned on by a switch so that a particular pattern is presented to an observer. The intensity of the ratio of red to green lights is divided into a number of categories, representing different types of color vision. The yellow lights are used for providing a spectral yellow color background whereas the red and green lights, in combination, provide a mixture of red and green for the different patterns. The different lights have different brightnesses, although the average intensity of the yellow color background would be equal to the average intensity of the chosen pattern, provided that the ratio of red to green colors has been carefully calibrated. Upon presentation of the thus calibrated pattern to an observer, depending on whether the observer can discern the pattern, the type of color vision the observer has can easily be ascertained.

Therefore, without ay action on the part of the patient observer, other than acknowledging whether a pattern is seen on the display, there is provided by the present invention and easy to use device that can also accurately measure the type of color vision an observer has.

Furthermore, the present invention device is able to prevent cheating by the patient observer since different patterns can be effected and the brightnesses of the different lights are not the same.

BRIEF DESCRIPTION OF THE DRAWINGS

FIG. 1 is a semi-block diagram illustration of the present invention;

FIG. 2a depicts a first pattern on the display of the present invention;

DETAILED DESCRIPTION OF THE INVENTION

Referring to the figures, and more particularly to FIG. 1, the essential components of the present invention color vision tester are illustrated. It should be emphasized that each of the shown circuits is conventional and is made from parts which are readily available. As shown, the present invention color vision tester includes a display 2, which may be comprised of a circuit board or some other means by which projection of light may be made. For example, if light emitting diodes (LEDs) are used, display 2 is a circuit board on which the LEDs may be mounted. Alternatively, if fiber optics are used, then display 2 may be a receptive plate for holding the ends of the fiber optic cables. Further, it should be noted that different types of light means may also be used. In any event, a representative display that has a plurality of light means, represented by circles, is shown in FIG. 2a.

Figure 2B:
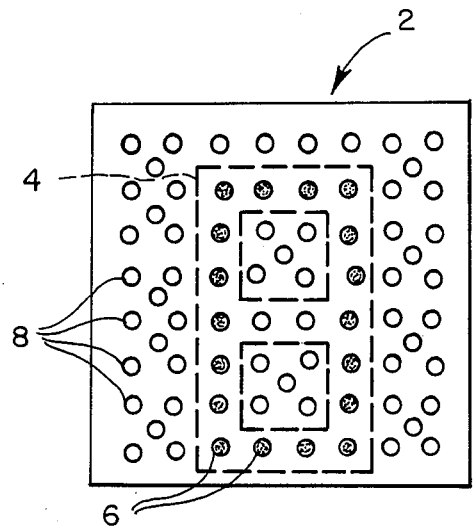
FIG. 2b shows a different pattern on the same display of the present invention.
Figure 3A:
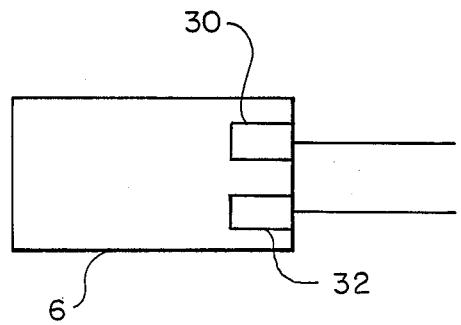
FIG. 3a is an illustration of a combination LED light depicted in FIGS. 2a and 2b.
Figure 3B:
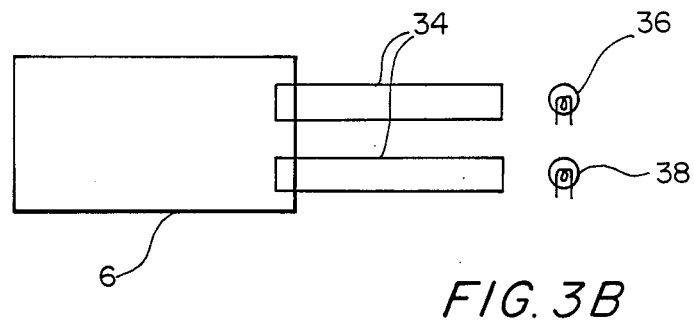
FIG. 3b is an illustration of a combination fiber optics light depicted in FIGS. 2a and 2b.

Consider FIG. 2a in conjunction with FIG. 2b. For the sake of simplicity, only two patterns, one in FIG. 2a representing a symbol A and one in FIG. 2b representing a symbol O, are shown by means of the darkened circles, representing selected light means. It should be noted that each of the patterns is formulated from a plurality of lights outlined by dash lines in the form of a figure 8, designated 4. Each of the lights within dash lines 4, for example designated as 6, is made of combined red and green spectral lights. For example, light 6 may be comprised of a combination of red LED 30 and green LED 32 or fiber optics 34 with red and green light sources 36 and 38. See FIGS. 3a and 3b. Other similar combinations may also be applicable. Thus, light 6 is actually a mixture of red and green lights; and the intensity of light 6 is dependent on a predetermined inverse relationship between the green and red spectral lights. In other words, the brightness of light 6 (perceived by an observer) would remain the same even though the amount of red to green spectral lights would change. For example, if the amount of green spectral light is decreased ten percent, there would be a ten percent increase in the amount of red spectral light. The amount of red to green spectral lights, although can be adjusted manually, is adjusted automatically in a conventional circuit, to be discussed hereinbelow, which has precalibrated ratios of the amount of red to green spectral lights.

As can be seen, there are a plurality of patterns which may be obtained from the lights within dash lines 4. For example, aside from the pattern A and the pattern O of FIG. 2a and FIG. 2b, respectively, patterns representing symbols P, 8, H, and others may also be obtained from within dash lines 4. Randomly distributed throughout the display and outside of dash lines 4 are a number of yellow lights, designated by 8. It should be appreciated that if all the lights are turned on and no attention is paid to the dash lines and the darkened circles within dash lines 4, no particular pattern would be seen on display 2. The types of lights and their respective uses, in terms of differentiating the different types of color vision, will be discussed hereinunder after an overall discussion of the present invention color tester is given.

Returning to FIG. 1, presuppose that mounted on display 2 are a plurality of lights 10, which represent, in actuality, lights 6 and 8 of FIGS. 2a and 2b. For this embodiment, only ten lights 10 are shown. It should be appreciated that this number was arbitrarily chosen for illustration purposes only. It should further be noted that these lights may be comprised of LEDs, fiber optics, or other known light means. As shown, each of lights 10 is connected by means of a wire (or cable) 12a to 12h to a coupler 14. The coupler is in turn connected to a pattern select circuit 16 and a ratio of red to green intensity control switch circuit 18. A power and control circuit 20 is connected to select circuit 16 and switch circuit 18. As was mentioned earlier, each of these circuits is conventional. For example, for the instant invention, switch circuit 18 may be made up of a five-way switch, each position of which being equated with a particular calibrated intensity ratio of red to green lights, with each intensity ratio corresponding to a specific type of color vision.

Elaborating, consider the following: Position 1 of the switch may be calibrated to a setting which corresponds to what a normal person would see. Thus, if the intensity of the ratio of red to green lights is set to position 1, a normal person, a protanope and a deuteranope would not be able to differentiate the pattern from the background yellow lights, as the mixture of red and green spectral lights would appear to be the same as the background yellow lights. On the other hand, a protanomalous trichromat and a deuteranomalous trichromat would be able to see the pattern. If position 2 of the switch is then set to a deuteranopic setting, everyone but a deuteranope would be able to see the pattern. Likewise, the third setting on the switch may be calibrated for a protanope so that everyone but a protanope may discriminate the pattern from the background. Continuing, position 4 of the switch may be calibrated to allow everyone but a deuteranope or a deuteranomalous trichromat to see the pattern. Finally, the final position of the switch may be calibrated to a setting which would allow everyone but a protanope or a protanomalous trichromat to see the pattern. Thus, by switching on a particular pattern of green and red lights and by setting the intensity of these red and green lights to a proper calibrated ratio by means of the different positions of switch circuit 18, different types of color vision can be ascertained.

To select the particular pattern, pattern select circuit 16 is used. Pattern select circuit 16 may be no more than a multiplexer, and associated circuitries, that would route the power provided by power and control circuit 20 to particular lights 10. Coupler 14 is used to impart to the chosen lights 10 the selected ratio of red to green intensity. Power and control circuit 20 supplies power to both pattern select circuit 16 and switch circuit 18. In addition, current from power and control circuit 20 is used to energize background yellow lights 8 and to maintain the same in various degrees of brightness during the course of testing. The combined red and green lights, likewise, except for the protanopic setting, are maintained in various degrees of brightness. This is to ensure that a patient observer, other than in the protanopic setting, will not be able to discriminate the pattern from the background by looking at the brightness of the lights. In a protanopic setting, however, the combined red and green lights would become so bright that the pattern will be brighter than the background lights.

When using LEDs as the light source, in the event that the physical attributes such as the size and shapes of the yellow, red and green LEDs are different, in order to ensure that an observer cannot make out the selected pattern by distinguishing the attributes, and therefore discering the locations, of the combined red and green LEDs from the background LEDs, a diffuser lens 22 is placed in front of display 2. Lens 22 not only obscures the outline of the different LEDs, it also diffuses the lights so that the subject observer cannot discriminate the particular pattern by recognizing the different types of LEDs.

In operation, a patient observer is placed in front of display 2. The clinician or tester would then activate the power and control circuit 20, thereby supplying power to both pattern select circuit 16 and switch circuit 18, as well as background yellow lights 8, which have different brightnesses maintained throughout the test. By means of pattern select circuit 16, a particular pattern is chosen from within dash lines 4 by activating the corresponding combined red and green lights 6. For example, patterns A and O, per FIGS. 2a and 2b, respectively, may be chosen. In order to make sure that the observer is not able to discriminate the pattern by zeroing in on the brightness of the lights, the average intensity of the red and green lights is made equal to the average intensity of the yellow background lights. Also, the brightness of the red and green lights would vary.

For the test itself, the patient observer is presented with the selected pattern at a first position setting of switch circuit 18. At this setting, only a protanomalous trichromat or a deuteranomalous trichromat would be able to see the pattern. At the second switch position, everyone but the deuteranope is able to see the pattern. Thus, if an observer is not able to see the pattern in the first position and yet was able to see the pattern in the second position, then by process of elimination, it would be safe to say that the observer is either a normal or a protanope. Next, the switch is placed in the third position where everyone but a protanope is able to discern the pattern. At this position, if the same observer is still able to see the pattern, he would be classified as a normal.

On the other hand, if the observer is unable to see the pattern, then he is classified as a protanope. Similarly, if at this position, an observer who was unable to see the pattern in the first and second positions is now able to see the pattern, he would be classified as a deuteranope. Continuing, if the switch is set to position 4, an observer who is either a deuteranope or a deuteranomalous trichromat would not be able to see the pattern. At position 5, the pattern would not be visible to either a protanope or a protanomalous trichromat. Therefore, by setting the intensity of the ratio of red to green lights to the different calibrations by means of the different switch positions, the type of color vision of an observer could easily be discerned by process of elimination without active participation on the part of the observer. Furthermore, the present color vision tester is able to pinpoint the type of color vision deficiency, if any, the oberserver has.

It should be appreciated that, instead of using five positions with five different ratios of red to green light settings, additional positions or settings, or for that matter, a variable switching circuit which can provide for continuous variation of red to green light ratios, can be added to or used for this color vision tester. Needless to say, if a continuous variable switching circuit is used, the degree of deficiency within a particular color vision can be precisely pinpointed.

Inasmuch as the present invention is subject to many variations, modifications, and changes in detail, it is intended that all matter described throughout this specification and accompanying the drawings be interpreted as illustrative and not in a limiting sense. Accordingly, it is intended that the invention be limited only by the spirit and scope of the appended claims.

I claim:

1. Apparatus for evaluating color vision of a human subject comprising:
   a display;
   a plurality of spectral yellow light means for providing randomly spaced background luminance in the yellow color spectrum on the display;
   a plurality of combination red and green light means interspersed with the spectral yellow light means for providing a mixture luminance in the red and green color spectrums on the display, the red and green light means forming a plurality of prearranged patterns on the display;
   power means for driving the light means and for controlling the luminance of the respective light means;
   means working cooperatively with the power meas for variably controlling respective red and green luminance of the mixture luminance provided by the combination red and green light means in a predetermined inverse relationship;
   means working cooperatively with the power means for selecting from among the plurality of prearranged patterns a particlar pattern for displaying to the subject, the particular pattern being chosen by activating a predetermined number of the combination red and green light means;
   wherein, by determining if the subject is able to discern the displayed pattern and by determining the inverse relationship of the respective red and green luminance set for the pattern, the type of color vision of the subject is ascertained.

2. Apparatus according to claim 1, further comprising:
   means for regulating the intensity of the respective light means luminance, differences in the intensity corresponding to different degrees of color deficiency, so that by varying the intensity, the degree of color deficiency of the subject is ascertained.

3. Apparatus according to claim 1, wherein the light means are LEDs.

4. Apparatus according to claim 1, further comprising means positioned in front of the display for obscuring the actual light means from view and for diffusing the luminance from the light means so that the subject cannot discriminate the particular pattern by differentiating the spectral yellow light means from the combination red and green light means.

5. Apparatus according to claim 1, wherein the light means are fiber optics.

6. Apparatus according to claim 1, wherein the selecting means comprises a circuitry for turning the light means on and off.

7. Apparatus for evaluating color vision of a human subject, comprising:
   a display;
   a plurality of spectral yellow light means for providing luminance in the yellow color spectrum on the display;

a plurality of red light means for providing luminance in the red color spectrum on the display;

a pluralty of green light means for providing luminance in the green color spectrum on the display, the green light means and the red light means interspersed with the spectral yellow light means and combining visually for forming a plurality of patterns having a mixture red and green luminance on the display and the spectral yellow light means being located randomly on the display for providing background yellow luminance for the patterns;

means for providing power to the light means;

means working cooperatively with the power means for variably controlling the luminance of the light means, the variable control means further variably regulating respective red and green luminance of the mixture red and green luminance in a predetermined inverse relationship so as to form multiple combinations of mixture red and green luminance, the multiple mixture combination corresponding to different degrees of color vision deficiency;

means working cooperatively with the power means for selectively turning on and off predetermined red and green light means so as to elect a particular pattern from the plurality of patterns for viewing by the subject;

wherein the type of color vision of the subject is ascertained by determining if the subject is able to discern the pattern from the background yellow luminance and by determining the combination of mixture red and green luminance for the particular pattern.

8. Apparatus according to claim 7, further comprising means positioned in front of the display for obscuring the actual light means from view and for diffusing the luminance from the light means so that the subject cannot discriminate the particular pattern by differentiating the spectral yellow light means from the combination red and green light means.

9. Apparatus according to claim 8, wherein the light means are LEDs mounted on the display.

10. Apparatus according to claim 8, wherein the light means are fiber optics.

11. Method of evaluating color vision of a human subject, comprising the steps of:
  (a) placing the subject in front of a display having a plurality of spectral yellow, red and green light means providing luminance in the yellow, red and green color spectrums respectively, the red and green light means being interspersed with the spectral yellow light means and forming a plurality of patterns on the display, the spectral yellow light means being located randomly on the display for providing background yellow luminance for the patterns;
  (b) activating power means for selectively turning on a predetermined number of the combined red and green light means to provide a particular pattern of mixture red and green luminance from the plurality of patterns for viewing by the subject;
  (c) setting respective red and green luminance of the mixture red and green luminance in a predetermined inverse relationship, the respective luminance varying at different inverse ratios, each inverse ratio corresponding to a type of color vision;
  (d) determining if the subject is able to discern the mixture red and green luminance pattern from the yellow luminance background;
  (e) repeating steps (b) and (c) until the subject discerns the pattern from the yellow luminance background for ascertaining the type of color vision the subject has.

12. Method according to claim 11, further comprising the step of:
  positioning an optical means in front of the display for obscuring the actual light means from view and for diffusing the luminance from the light means so that the subject cannot discriminate the particular pattern by differentiating the spectral yellow light means from the combined red and green light means.

13. Apparatus for evaluating color vision of a human subject comprising:
  a display;
  a plurality of spectral yellow light means for providing randomly spaced background luminance in the yellow color spectrum on the display;
  a plurality of combination red and green light means interspersed with the spectral yellow light means for providing a mixture luminance in the red and green color spectrums on the display, the red and green light means forming at least one prearranged pattern on the display;
  power means for driving the light means and for controlling the luminance of the respective light means;
  means working cooperatively with the power means for variably controlling respective red and green luminance of the mixture luminance provided by the combination red and green light means in a predetermined inverse relationship;
  wherein, by determining if the subject is able to discern the displayed pattern and by determining the inverse relationship of the respective red and green luminance set for the pattern, the type of color vision of the subject is ascertained.

14. Apparatus according to claim 13, further comprising:
  means for regulating the intensity of the respective light means luminance, differences in the intensitty corresponding to different degrees of color deficiency, so that by varying the intensity, the degree of color deficiency of the subject is ascertained.

15. Apparatus according to claim 13, wherein the light means are LEDs.

16. Apparatus according to claim 13, wherein the light means are fiber optics.

17. Apparatus for evaluating color vision of a human subject, comprising:
  a display;
  a plurality of spectral yellow light means for providing luminance in the yellow color spectrum on the display;
  a plurality of red light means for providing luminance in the red color spectrum on the display;
  a plurality of green light means for providing luminance in the green color spectrum on the display, the green light means and the red light means interspersed with the spectral yellow light means and combining visually for forming at least one pattern having a mixture red and green luminance on the display and the spectral yellow light means being located randomly on the display for providing background yellow luminance for the pattern;
  means for providing power to the light means;

means working cooperatively with the power means for variably controlling the luminance of the light means, the variable control means further variably regulating respective red and green luminance of the mixture red and green luminance in a predetermined inverse relationship so as to form multiple combinations of mixture red and green luminance, the multiple mixture combinations corresponding to different degrees of color vision deficiency;

wherein the type of color vision of the subject is ascertained by determining if the subject is able to discern the pattern from the background yellow luminance and by determining the combination of mixture red and green luminance for the particular pattern.

18. Apparatus according to claim 17, further comprising means positioned in front of the display for obscuring the actual light means from view and for diffusing the luminance from the light means so that the subject cannot discriminate the particular pattern by differentiating the spectral yellow light means from the combination red and green light means.

19. Method of evaluating color vision of a human subject, comprising the steps of:
  (a) placing the subject in front of a display having a plurality of interspersed spectral yellow, red and green light means providing luminance in the yellow, red and green color spectrums, respectively, the red and green light means being combined to form at least one pattern on the display, the spectral yellow light means bein located randomly on the display for providing background yellow luminance for the pattern;
  (b) setting respective red and green luminance of the mixture red and green luminance in a predetermined inverse relationship, the respective luminance varying at different inverse ratios, each inverse ratio corresponding to a type of color vision;
  (c) determining if the subject is able to discern the mixture red and green luminance pattern from the yellow luminance background;
  (d) repeating steps (b) and (c) until the subject discerns the pattern from the yellow luminance background for ascertaining the type of color vision the subject has.

20. Method according to claim 19, further comprising the step of:
  positioning an optical means in front of the display for obscuring the actual light means from view and for diffusing the luminance from the light means so that the subject cannot discriminate the particular pattern by differentiating the spectral yellow light means from the combined red and green light means.

* * * * *

UNITED STATES PATENT AND TRADEMARK OFFICE
CERTIFICATE OF CORRECTION

PATENT NO. : 4,848,898
DATED : July 18, 1989
INVENTOR(S) : Robert W. Massof

It is certified that error appears in the above-identified patent and that said Letters Patent is hereby corrected as shown below:

Column 1, line 38, change "equire" to --require--;

line 41, before "color" insert --inherited--;

line 60, change "give" to --given--;

line 64, change "diclosed" to --disclosed--.

Column 2, line 50, change "ay" to --any--;

line 53, change "and" to --an--.

Column 5, line 61, change "oberserver" to --observer--.

Column 6, line 26, change "meas" to --means--.

Column 8, line 43, change "intensitty" to --intensity--.

Column 10, line 3, change "bein" to --being--.

Signed and Sealed this

Fifteenth Day of May, 1990

Attest:

HARRY F. MANBECK, JR.

*Attesting Officer*   *Commissioner of Patents and Trademarks*